United States Patent [19]

Bonne et al.

[11] 4,108,993
[45] Aug. 22, 1978

[54] 3-OXO-5,6-DIHYDRO-1,2,4-OXADIAZINES USEFUL AS ANTIANDROGENIC AGENTS

[75] Inventors: Claude Bonne, Bry-sur-Marne; Jacques Perronnet, Paris; André Teche, Nanterre, all of France

[73] Assignee: Roussel Uclaf, Paris, France

[21] Appl. No.: 729,763

[22] Filed: Oct. 5, 1976

[30] Foreign Application Priority Data

Oct. 15, 1975 [FR] France .................. 75 31566

[51] Int. Cl.² .......................... A01N 9/00; A01N 9/22
[52] U.S. Cl. ........................ 424/248.57; 424/248.52
[58] Field of Search ............ 260/244 R; 424/248.52, 424/248.54, 248.55, 248.56, 248.57

[56] References Cited

U.S. PATENT DOCUMENTS

| | | | |
|---|---|---|---|
| 3,238,200 | 3/1966 | Bernstein et al. | 260/244 R |
| 3,537,839 | 11/1970 | Steinbrunn et al. | 260/244 R |
| 3,625,968 | 12/1971 | Zschocke et al. | 260/244 R |
| 3,696,099 | 10/1972 | Makula et al. | 260/244 R |
| 3,829,419 | 8/1974 | Weir | 424/248.54 |

FOREIGN PATENT DOCUMENTS

| | | | |
|---|---|---|---|
| 2,039,472 | 1/1971 | France | 260/244 R |
| 2,097,085 | 3/1972 | France | 260/244 R |
| 2,015,863 | 10/1970 | Fed. Rep. of Germany | 260/244 R |

Primary Examiner—Albert T. Meyers
Assistant Examiner—D. W. Robinson
Attorney, Agent, or Firm—Hammond & Littell

[57] ABSTRACT

Antiandrogenic compositions comprising an effective amount of at least one compound of the formula

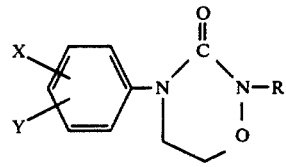

wherein X and Y are individually selected from the group consisting of hydrogen, halogen, —CF₃, —NO₃ and alkylthio of 1 to 4 carbon atoms and R is selected from the group consisting of hydrogen, alkyl of 1 to 6 carbon atoms, phenyl, benzyl and hydroxymethyl and an inert pharmaceutical carrier and a method of inducing antiandrogenic activity in warm-blooded animals as well as novel oxadiazines of formula I with the proviso that when R is other than benzyl or hydroxymethyl at least one of X and Y is alkylthio of 1 to 4 carbon atoms.

4 Claims, No Drawings

3-OXO-5,6-DIHYDRO-1,2,4-OXADIAZINES USEFUL AS ANTIANDROGENIC AGENTS

STATE OF THE ART

French Pat. Nos. 2,039,472 and 2,097,085 describe similar oxadiazines. The first patent describes their use as bactericides, algicides and fungicides and the second patent describes their use as herbicides.

OBJECTS OF THE INVENTION

It is an object of the invention to provide novel oxadiazines.

It is another object of the invention to provide novel antiandrogenic compositions and to provide a novel method of inducing antiandrogenic activity in warm-blooded animals.

These and other objects and advantages of the invention will become obvious from the following detailed description.

THE INVENTION

The novel antiandrogenic compositions of the invention are comprised of at least one compound of the formula

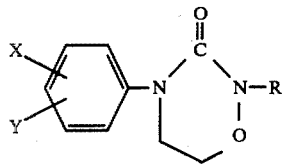

wherein X and Y are individually selected from the group consisting of hydrogen, halogen, $-CF_3$, $-NO_3$ and alkylthio of 1 to 4 carbon atoms and R is selected from the group consisting of hydrogen, alkyl of 1 to 6 carbon atoms, phenyl, benzyl and hydroxymethyl and an inert pharmaceutical carrier.

Examples of halogens and alkylthio groups of X and Y are chlorine, bromine, methylthio, ethylthio, propylthio, isopropylthio, butylthio, sec-butylthio and tert.-butylthio. Examples of alkyl groups of R are methyl, ethyl, propyl, isopropyl, butyl, sec-butyl, tert.-butyl, pentyl and tert.-pentyl.

The preferred compositions of the invention have a local antiandrogenic activity and have at least one compound of formula I wherein R is methyl and X and Y are chlorine, nitro or $-CF_3$. Two preferred oxadiazines are 2-methyl-4-(3',4'-dichlorophenyl)-3-oxo-5,6-dihydro-1,2,4-oxadiazine and 2-methyl-4-(3'-trifluoromethyl-4'-nitrophenyl)-3-oxo-5,6-dihydro-1,2,4-oxadiazine.

The compositions have a remarkable antiandrogenic activity, particularly when applied locally. The oxadiazines of formula I inhibit the effects of androgens on the peripheric receptors without causing injury to the normal functioning of hypophysis. They are useful for medicines for adolescents without fear of arresting their growth and for adults without having fear of certain effects of chemical castration. They are notably useful for treatment of local affections due to a hyperandrogenicity such as hirsutism, acne, seborrhea or hyperpilosity as well as be useful in the veterinary field.

The compositions may be in the usual forms, particularly those useful for topical applications such as solutions, emulsions, creams, pomades and lotions.

The inert pharmaceutical carrier may be those ordinarily used as excipients such as aqueous or non-aqueous vehicles, lactose, starch, fatty bodies of animal or vegetable origin, paraffinic derivatives, glycols, preservatives, diverse wetting agents, dispersants and emulsifiers. An example of the usual dose of oxadiazine is 5 to 10% in a pomade and 1 to 3 times per day. The compositions may also be used in cosmetology.

The novel method of the invention of inducing antiandrogenic activity in warm-blooded animals, including humans, comprises administering to warm-blooded animals an effective amount of at least one oxadiazine of formula I. The compounds are preferably topically administered.

The novel oxadiazines of the invention are those compounds of formula I with the proviso that when R is other than benzyl or hydroxymethyl, at least one of X and Y is alkylthio of 1 to 4 carbon atoms. Particularly preferred are 2-methyl-4-(4'-methylthio-3'-trifluoromethylphenyl)-3-oxo-5,6-dihydro-1,2,4-oxadiazine, 2-benzyl-4-(3',4'-dichlorophenyl)-3-oxo-5,6-dihydro-1,2,4-oxadiazine and 2-hydroxymethyl-4-(3',4'-dichlorophenyl)-3-oxo-5,6-dihydro-1,2,4-oxadiazine.

Other novel oxadiazines of formula I are those where R is methyl and the phenyl ring is substituted with 2',4'- or 3',5'-dichloro or with $-CF_3$ in the 3'-position and $-NO_2$ or $-Cl$ in the 4'-position or with $-NO_2$ in the 3'-position. Also, when R is phenyl, hydrogen or n-pentyl, the phenyl ring attached to nitrogen atom in the 4-position of oxadiazine ring is substituted with 3',4'-dichloro and especially 2-methyl-4-(3'-trifluoromethyl-4'-nitrophenyl)-3-oxo-5,6-dihydro-1,2,4-oxadiazine.

A process for the preparation of oxadiazines of the formula

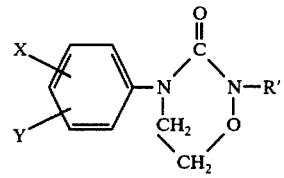

wherein X and Y have the above definition and R' is alkyl of 1 to 6 carbon atoms, phenyl or benzyl with at least one of X and Y being alkylthio of 1 to 4 carbon atoms when R' is other than benzyl comprises reacting a compound of the formula

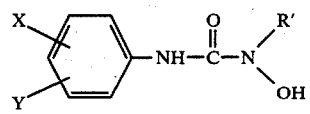

with a 1,2-dihaloethane to obtain the compound of formula Ia.

The preferred 1,2-dihaloethane is 1,2-dichloroethane although 1,2-dibromoethane is equally useful. The reaction is preferably effected in a polar solvent such as dimethylsulfoxide but other polar solvents such as dimethylformamide or hexamethylphosphorotriamide may be used. The reaction is preferably effected in the presence of a basic salt such as potassium carbonate but equally useful are sodium carbonate or a tertiary amine base such as triethylamine.

A process to prepare the compounds of formula I wherein R is hydrogen comprises reacting a compound of the formula

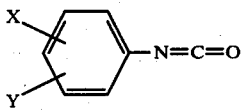

wherein X and Y have the above definition with 0-(2-bromoethyl)-hydroxylamine to obtain a compond of the formula

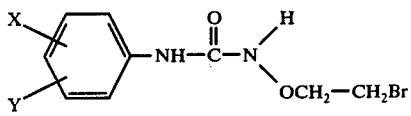

which is treated with a base to effect cyclization to obtain the desired compound of formula I.

In a preferred mode, the addition of 0-(2-bromoethyl)-hydroxylamine is effected in the presence of a base such as triethylamine but other bases such as sodium carbonate or potassium carbonate may also be used and the reaction is effected in a polar solvent such as dimethylformamide but other polar solvents such as dimethylsulfoxide or hexamethylphosphorotriamide may be used. The cyclization is effected in the presence of a base such as potassium carbonate but equally useful are sodium carbonate or tertiary amine bases such as triethylamine and a polar solvent such as acetone is used but other solvents such as ethylacetate or methyl ethyl ketone may be used.

Another process for the preparation of compounds of formula I wherein R is hydrogen comprises subjecting a compound of the formula

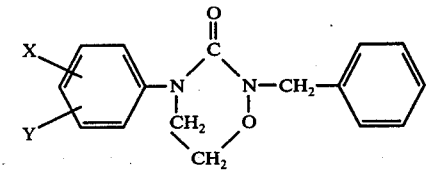

to hydrogenolysis in the presence of a catalyst. The prefered hydrogenolysis catalyst is palladized carbon in acetic acid but other catalysts such as platinum or other supports such as barium sulfate with other solvents such as methanol or ethanol may be used.

A process for the preparation of a compound of formula I wherein R is hydroxymethyl comprises reacting a compound of formula I wherein R is hydrogen with formic aldehyde. The reaction is preferably effected in dioxane in the presence of sodium acetate but other salts such as sodium or potassium carbonate or bicarbonate and other solvents such as tetrahydrofuran may be used.

A process for the preparation of a compound of formula I wherein X and Y are other than alkylthio and R is phenyl or alkyl of 1 to 6 carbon atoms comprises reacting a 1,2-dihaloethane with a compound of the formula

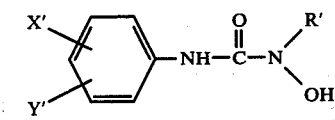

wherein X' and Y' are hdrogen, halogen, —CF$_3$ or —NO$_2$ and R' is phenyl or alkyl of 1 to 6 carbon atoms.

The preferred 1,2-dihaloethane is 1,2-dichloroethane although 1,2-dibromoethane is equally useful. The reaction is preferably effected in a polar solvent such as dimethylsulfoxide but other polar solvents such as dimethylformamide or hexamethylphosphorotriamide may be used. The reaction is preferably effected in the presence of a basic salt such as potassium carbonate but equally useful are sodium carbonate or a tertiary amine base such as triethylamine.

The products of formula II may be prepared by reacting an isocyanate of the formula

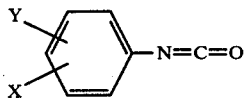

with a hydroxylamine of the formula R'-NHOH. The said isocyanates, if not known, may be prepared by reacting phosgene with the corresponding aniline.

The preparation of an aniline substituted with an alkylthio group is illustrated in the examples and thus permits the preparation of other anilines carrying this substituent by reacting a mercaptan with a nitrobenzene having a chlorine substituent and then reducing the nitro group.

In the following examples there are described several preferred embodiments to illstrate the invention. However, it is to be understood that the invention is not intended to be limited to the specific embodiments.

EXAMPLE 1

2-methyl-4-(2',4'-dichlorophenyl)-3-oxo-5,6-dihydro-1,2,4-oxadiazine

A mixture of 11 g of N-methyl-N-hydroxy-N'-(2,4-dichlorophenyl)-urea, 55 g of potassium carbonate and 66 ml of dimethylsulfoxide was stirred for 20 minutes at 20° C and then 11 g of dichloroethane were added. The mixture was stirred for 16 hours at 20°–25° C and was then poured into water. The mixture was vacuum filtered and the recovered precipitate was taken up in ethyl acetate. The solution was dried and evaporated to dryness under reduced pressure. The residue was crystallized from isopropyl ether to obtain 8 g of 2-methyl-4-(2',4'-dichlorophenyl)-3-oxo-5,6-dihydro-1,2,4-oxadiazine melting at 94°–95° C.

Analysis: $C_{10}H_{10}Cl_2N_2O_2$: Calculated: %C 46.0 %H 3.86 %Cl 27.16 %N 10.73: Found: 46.0 3.9 27.1 10.6.

EXAMPLE 2

2-methyl-4-(3',5'-dichlorophenyl)-3-oxo-5,6-dihydro-1,2,4-oxadiazine

STEP A: N-methyl-N-hydroxy-N'-(3,5-dichlorophenyl)-urea

A mixture of 10 g of N-methyl-hydroxylamine hydrochloride in 100 ml of chloroform was stirred while 18 ml of triethylamine were added at 0° C. Then, 20 g of 3,5-dichlorophenyl isocyanate in 30 ml of chloroform were added to the mixture at 10° to 15° C and the mixture was stirred for 5 hours at 20° C and was then distilled to dryness under reduced pressure. The residue was taken up in water and dried to obtain 22 g of N-methyl-N-hydroxy-N'-(3,5-dichlorophenyl)-urea melting at 131°–132° C.

STEP B: 2-methyl-4-(3',5'-dichlorophenyl)-3-oxo-5,6-dihydro-1,2,4-oxadiazine

Using the procedure of Example 1, a mixture of 16 g of the product of Step A, 80 g of potassium carbonate, 100 ml of dimethylsulfoxide and 16 g of dichloroethane was reacted to obtain 20 g of product. The latter was chromatographed over silica gel and was eluted with an 8-2 benzene-acetone mixture to obtain 12 g of 2-methyl-4-(3',5'-dichlorophenyl)-3-oxo-5,6-dihydro-1,2,4-oxadiazine melting at 105°–106° C.

Analysis: $C_{10}H_{10}Cl_2N_2O_2$: Calculated: %C 46.0 %H 3.86 %Cl 27.16 %N 10.73: Found: 45.8 3.9 27.0 10.5.

EXAMPLE 3

2-methyl-4-(4'-nitro-3'-trifluoromethylphenyl)-3-oxo-5,6-dihydro-1,2,4-oxadiazine STEP A: N-hydroxy-N-methyl-N'-(3'-trifluoro 4'-nitromethylphenyl)-urea 24 ml of triethylamine were added over 5 minutes to a stirred mixture of 15 g of N-methylhydroxylamine hydrochloride in 100 ml of chloroform cooled to 0° C and then 37.5g of 3-trifluoromethyl-4-nitrophenyl isocyanate were added at 20° to 25° C. The mixture was stirred at 20° C for 16 hours and was then poured into water. The mixture was vacuum filtered and the recovered crystals were dried under reduced pressure. The raw product was taken up in hot isopropyl ether and the solution was treated with activated carbon and was evaporated to dryness under reduced pressure to obtain 20 g of N-hydroxy-N-methyl-N'-(3'-trifluoromethyl-4'-nitrophenyl)-urea melting at 129°–130° C.

STEP B: 2-methyl-4-(3'-trifluoromethyl-4'-nitrophenyl)-3-oxo-5,6-dihydro-1,2,4-oxadiazine 15 g of dichloroethane were added at 20° C to a stirred mixture of 15 g of the product of Step A, 75 g of potassium carbonate and 90 ml of dimethylsulfoxide and the mixture was stirred at 20° C for 16 hours. The mixture was poured into ice water and the mixture was decanted. The oil was taken up in methylene chloride and the solution was washed with water, dried and evaporated to dryness under reduced pressure. The residue was chromatographed over silica gel and was eluted with an 8-2 benzene-acetone mixture to obtain 8 g of 2-methyl-4-(4'-nitro-3'-trifluoromethylphenyl)-3-oxo-5,6-dihydro-1,2,4-oxadiazine melting at 104°–105° C.

Analysis: $C_{11}H_{10}F_3N_3O_4$: Calculated: %C 43.28 %H 3.30 %N 13.77 %F 18.67; Found: 43.5 3.4 13.8 18.5.

EXAMPLE 4

2-phenyl-4-(3',4'-dichlorophenyl)-3-oxo-5,6-dihydro-1,2,4-oxadiazine

Using the procedure of Example 1, 40 g of N-(3',4'-dichlorophenyl)-N'-hydroxy-N'-phenyl-urea were reacted to obtain 28 g of 2-phenyl-4-(3',4'-dichlorophenyl)-3-oxo-5,6-dihydro-1,2,4-oxadiazine melting at 112°–113° C.

Analysis: $C_{15}H_{12}Cl_2N_2O_2$: Calculated: %C 55.74 %H 3.74 %Cl 21.94 %N 8.67: Found: 55.7 3.7 21.7 8.6.

EXAMPLE 5

4-(3',4'-dichlorophenyl)-3-oxo-5,6-dihydro-1,2,4-oxadiazine

STEP A: N-2-bromoethoxy-N'-(3,4-dichlorophenyl)-urea 11 g of triethylamine were added dropwise to a stirred mixture of 25 g of 0-(2-bromoethyl)-hydroxylamine hydrobromide and 250 ml of dimethylformamide at 20°–25° C and the mixture was vacuum filtered to remove triethylamine hydrobromide. 18.8 g of 3,4-dichlorophenyl isocyanate were added in small fractions and the mixture was stirred for 3 hours and was then poured into water. The mixture was extracted with methylene chloride and the extracts were evaporated to dryness under reduced pressure to obtain 11 g of N-2-bromoethoxy-N'-(3,4-dichlorophenyl)-urea melting at 126° C.

STEP B: 4-(3',4'-dichlorophenyl)-3-oxo-5,6-dihydro-1,2,4-oxadiazine

A mixture of 40 g of the product of Step A, 27 g of potassium carbonate and 400 ml of actone was stirred at 20°–25° C for 16 hours and the mixture was filtered. The filtrate was evaporated to dryness under reduced pressure to obtain, after crystallization from ethyl acetate, 5 g of 4-(3',4'-dichlorophenyl)-3-oxo-5,6-dihydro-1,2,4-oxadiazine melting at 152° C.

Analysis: $C_9H_8Cl_2N_2O_2$: Calculated: %C 43.75 %H 3.26 %Cl 28.70 %N 11.34: Found: 43.8 3.3 28.7 11.3.

EXAMPLE 6

2-methyl-4-(3'-nitrophenyl)-3-oxo-5,6-dihydro-1,2,4-oxadiazine

Using the procedure of Example 1, 30 g of N-methyl-N-hydroxy-N'-(3'-nitrophenyl)-urea were reacted to obtain 10 g of 2-methyl-4-(3'-nitrophenyl)-3-oxo-5,6-dihydro-1,2,4-oxadiazine which was chromatographed over silica gel and was eluted with a 7-3 benzene-acetone mixture to obtain a product melting at 107°–108° C.

Analysis: $C_{10}H_{11}N_3O_4$: Calculated: %C 50.63 %H 4.67 %N 17.71: Found: 50.6 4.6 17.8.

EXAMPLE 7

2-methyl-4-(4'-chloro-3'-trifluoromethylphenyl)-3-oxo-5,6-dihydro-1,2,4-oxadiazine STEP A: N-methyl-N-hydroxy-N'-(4'-chloro-3'-trifluoromethylphenyl)-urea 33 ml of triethylamine and then 44.3 g of 4-chloro-3-trifluoromethylphenyl isocyanate in 200 ml of chloroform were added to a mixture of 21 g of N-methyl hydroxylamine hydrochloride and 200 ml of chloroform at 0° C and the mixture was stirred at 20° C for 16 hours. The mixture was washed with water and was reduced to a volume of 100 ml under reduced pressure. The mixture was iced and vacuum filtered. The crystals were washed with water and dried to obtain 37 g of N-methyl-N-hydroxy-N'-(4'-chloro-3'-trifluoromethylphenyl)-urea melting at 114°–115° C.

STEP B: 2-methyl-4-(4'-chloro-3'-trifluoromethylphenyl)-3-oxo-5,6-dihydro-1,2,4-oxadiazine Using the procedure of Example 1, 30 g of the product of Step A were reacted to obtain 23 g of 2-methyl-4-(4'-chloro-3'-trifluoromethylphenyl)-3-oxo-5,6-dihydro-1,2,4-oxadiazine melting at 72°–73° C.

Analysis: $C_{11}H_{10}ClF_3N_2O_2$: Calculated: %C 44.83 %H 3.42 %F 19.34 %N 9.51: Found: 45.1 3.5 19.0 9.3.

EXAMPLE 8

2-methyl-4-(4'-methylthio-3'-trifluoromethylphenyl)-3-oxo-5,6-dihydro-1,2,4-oxadiazine STEP A: 4-methylthio-3-trifluoromethyl-nitrobenzene A mixture of 30 g of methyl mercaptan in 50 ml of ethanol was added at 10° C to a mixture of 12.5 g of sodium in 500 ml of ethanol and then 63 g of 3-trifluoromethyl-4-chloro-nitrobenzene were added thereto. The mixture stood at room temperature for 17 hours and was vacuum filtered. The recovered precipitate was washed with water and dried to obtain 22 g of 4-methylthio-3-trifluoromethyl-nitrobenzene melting at 158° C.

STEP B: 4-methylthio-3-trifluoromethyl-aniline 16.5 g of the product of Step A were added to a mixture of 110 ml of ethanol, 100 ml of water and 1 ml of 22° Bé hydrochloric acid and then 47 g of hematite iron were added thereto. The mixture was refluxed for 6 hours and was filtered hot. The filtrate was washed with methylene chloride and evaporated to dryness under reduced pressure to obtain 6 g of 4-methylthio-3-trifluoromethyl-aniline with a refractive index of $n_D^{22} = 1.553$.

STEP C: 4-methylthio-3-trifluoromethyl-phenyl isocyanate

A mixture of 6 g of the product of Step B in 60 ml of toluene was poured into 150 ml of toluene saturated with phosgene and the mixture was refluxed for 4 hours under a current of phosgene. The mixture stood at room temperature for 17 hours and was then evaporated to dryness under reduced pressure. The residue was extracted with isopropyl ether and was dissolved by heating. The mixture was iced and was vacuum filtered. The crystals were dried to obtain 3.4 g of 4-methylthio-3-trifluoromethylphenyl isocyanate melting at 40° C.

STEP D: N-(4-methylthio-3-trifluoromethylphenyl)-N'-methyl-N'-hydroxy-urea

A mixture of 3.4 g of the product of Step C in 34 ml of chloroform was added at 0° C to a mixture of 1.6 g of N-methyl-hydroxylamine hydrochloride, 16 ml of chloroform and 2.4 ml of triethylamine and the mixture stood at room temperature for 48 hours. The mixture was evaporated to dryness under reduced pressure and the residue was taken up in ether and was filtered to obtain 2.5 g of N-(4-methylthio-3-trifluoromethylphenyl)-N'-methyl-N'-hydroxy-urea melting at 125° C.

STEP E: 2-methyl-4-(4'-methylthio-3'-trifluoromethylphenyl)-3-oxo-5,6-dihydro-1,2,4-oxadiazine Using the procedure of Example 1, 2.5 g of the product of Step D were reacted and the product formed was chromatographed over silica gel and was eluted with a 9-1 methylene chloride-ethyl acetate mixture to obtain 0.9 g of 2-methyl-4-(4'-methylthio-3'-trifluoromethylphenyl)-3-oxo-5,6-dihydro-1,2,4-oxadiazine melting at 60° C.

Analysis: $C_{12}H_{13}F_3N_2O_2S$: Calculated: %C 47.05 %H 4.27 %N 9.14 %F 18.60 %S 10.46: Found: 46.9 4.4 9.2 18.4 10.6.

EXAMPLE 9

2-benzyl-4-(3',4'-dichlorophenyl)-3-oxo-5,6-dihydro-1,2,4-oxadiazine

STEP A: N-hydroxy-N-benzyl-N'-(3',4'-dichlorophenyl)-urea

A mixture of 13.3 g of N-benzyl-hydroxylamine in 260 ml of anhydrous benzene was added to a solution of 20.3 g of 3,4-dichlorophenyl isocyanate in 400 ml of anhydrous benzene and the mixture was refluxed for half an hour and then was cooled with stirring. The mixture was vacuum filtered and the recovered crystals were empasted with benzene to obtain 28.2 g of N-hydroxy-N-benzyl-N'-(3',4'-dichlorophenyl)-urea melting at 157° C.

STEP B: 2-benzyl-4-(3',4'-dichlorophenyl)-3-oxo-5,6-dihydro-1,2,4-oxadiazine

A mixture of 15.5 g of the product of Step A, 77.5 g of potassium carbonate and 93 ml of dimethylsulfoxide was stirred for 30 minutes and 15.5 g of dichloroethane were added. The mixture was stirred for 16 hours at room temperature and was poured into water. The mixture was vacuum filtered and the recovered precipitate was washed with water. The product was dissolved in ethyl acetate and the solution was dried, filtered and evaporated to dryness. The 18 g of crystalline product were crystallized from isorpopyl ether to obtain 14.5 g of 2-benzyl-4-(3',4'-dichlorophenyl)-3-oxo-5,6-dihydro-1,2,4-oxadiazine melting at 76° C.

Analysis: $C_{16}H_{14}Cl_2N_2O_2$: Calculated: %C 56.99 %H 4.18 %Cl 21.02 %N 8.30: Found: 56.7 4.3 21.0 8.3.

EXAMPLE 10

2-pentyl-4-(3',4'-dichlorophenyl)-3-oxo-5,6-dihydro-1,2,4-oxadiazine

STEP A: N-pentyl-N-hydroxy-N'-(3,4-dichlorophenyl)-urea

A mixture of 16 g of N-pentyl-hydroxylamine in 80 ml of isopropyl ether was added to 29.2 g of 3,4-dichlorophenyl isocyanate in 500 ml of isopropyl ether and the mixture was stirred for 16 hours and was evaporated to dryness. The residue was taken up in petroleum ether to obtain 45 g of N-pentyl-N-hydroxy-N'-(3,4-dichlorophenyl)-urea melting at 88° C.

STEP B: 2-pentyl-4-(3',4'-dichlorophenyl)-3-oxo-5,6-dihydro-1,2,4-oxadiazine

Using the procedure of Example 1, 20 g of the product of Step A were reacted and the product was chromatographed over silica gel and was eluted with an 8-2 cyclohexane-ethyl acetate mixture to obtain 13 g of 2-pentyl-4-(3',4'-dichlorophenyl)-3-oxo-5,6-dihydro-1,2,4-oxadiazine melting at <40° C.

Analysis: $C_{14}H_{18}Cl_2N_2O_2$: Calculated: %C 53.01 %H 5.72 %Cl 22.35 %N 8.83: Found: 52.7 5.7 22.6 8.7.

EXAMPLE 11

2-hydroxy methyl-4-(3',4'-dichlorophenyl)-3-oxo-5,6-dihydro-1,2,4-oxadiazine 300 ml of an aqueous solution of 30% formic aldehyde were added to a mixture of 30 g of 4-(3',4'-dichlorophenyl)-3-oxo-5,6-dihydro-1,2,4-oxadiazine, 30 g of anhydrous sodium acetate and 300 ml of dioxane and then the mixture was stirred for 2 hours at 20°–25° C and was acidified. The mixture was extracted with ethyl acetate and the extracts were dried and evaporated to dryness under reduced pressure. The residue was taken up in isopropyl ether and the mixture was vacuum filtered. The recovered solids were dried to obtain 30 g of 2-hydroxymethyl-4-(3',4'-dichlorophenyl)-3-oxo-5,6-dihydro-1,2,4-oxadiazine melting at 134° C.

Analysis: $C_{10}H_{10}N_2Cl_2O_3$: Calculated: %C 43.34 %H 3.64 %N 10.11 %Cl 25.29 %O 17.32: Found: 43.4 3.8 10.0 25.3

EXAMPLE 12

4-(3',4'-dichlorophenyl)-3-oxo-5,6-dihydro-1,2,4-oxadiazine

Hydrogen was passed through a mixture of 3.37 g of 2-benzyl-4-(3',4'-dichlorophenyl)-3-oxo-5,6-dihydro-1,2,4-oxadiazine, 70 ml of acetic acid, 680 mg of animal charcoal and 0.6 ml of a 20% palladium chloride solution until absorption ceased and the mixture was filtered. The filter was washed with acetic acid and the filtrate was poured into ice water. The mixture was extracted with methylene chloride and the organic extracts were dried and evaporated to dryness. The crystalline product was taken up in isopropyl ether to obtain 2.37 g of 4-(3',4'-dichlorophenyl)-3-oxo-5,6-dihydro-1,2,4-oxadiazine melting at 152° C.

EXAMPLE 13

A pomade for topical application was prepared from 100 mg of 2-methyl-4-(3'-trifluoromethyl-4'-nitrophenyl)-3-oxo-5,6-dihydro-1,2,4-oxadiazine and sufficient excipient for a total weight of 1 g.

A dermatological composition was prepared consisting of 10% by weight of 2-methyl-4-(3'-trifluoromethyl-4'-nitrophenyl)-3-oxo-5,6-dihydro-1,2,4-oxadiazine, 30% by weight of propylene carbonate, 8% by weight of Eutanol and 52% by weight of ethanol.

PHARMACOLOGICAL STUDY

The following products were used in the pharmacological tests: product A- 2-methyl-4-(3',4'-dichlorophenyl)-3-oxo-5,6-dihydro-1,2,4-oxadiazine; product B- 2-methyl-4-(4'-chlorophenyl)-3-oxo-5,6-dihydro-1,2,4-oxadiazine; product C- 2-ethyl-4-(3',4'-dichlorophenyl)-3-oxo-5,6-dihydro-1,2,4-oxadiazine.

A. Inhibition of prostatic incorporation of radioactivity after injection of a dose of trace $H^3$-testosterone in castrated rats.

Groups of 3 male rats of the Sprague-Dawley SPF strain weighing 70 ± 10 g were castrated 24 hours before receiving an intraperitoneal injection of 5 mg of the test product. 16 hours later, the animals received an intermuscular injection of 10μ Ci/100 g of 1α³-H-testosterone (26 Ci/mmol) in an alcholic solution and the animals were killed one hour after the hormone injection. The ventral prostate was removed, rinsed with an isotonic sodium chloride solution, weighed and then was solubilized in 1 ml of Soluene (strong organic base in toluene). The radioactivity of the samples were measured after addition of 15 ml of sparkling liquid and the results are reported in Table I as a percentage of inhibition of testosterone incorporation. dpm/mg = disintegration per minute per mg of fresh prostatic tissue.

TABLE I

| Product | Incorporation dpm/mg | % of Inhibition |
|---|---|---|
| Controls | 162.5 ± 1.5 | — |
| A | 63.9 ± 4.8 | 61 |
| B | | 33 |
| C | | 40 |
| Example 1 | | 41 |
| Example 2 | | 61 |
| Example 3 | | 68 |
| Example 4 | | 50 |
| Example 5 | | 35 |
| Example 6 | | 37 |
| Example 7 | | 44 |

B. Local antiandrogenic activity — test with organotypic culture of prostate

Rats castrated 24 hours earlier were anesthesied with ether and the prostate was aseptically removed and was rinsed with Tyrode solution at 0° to 4° C. The prostate tissue was divided into fragments measuring about 2 × 3 × 3 mm by cutting the stroma separating the alveolus formations. The fragments were then placed in culture by the method of Lasnikzki [J. Endocr., Vol. 30 (1964), p. 325] slightly modified in 2 ml of modified synthetic 199 medium (Pasteur Institute) containing 100 UI/ml of penicillin G and 0.1 mg/ml of streptomycin. The explants thus obtained were cultivated with one part in a medium without hormone (controls), one part in the presence of an androgenic hormone (androstanolone) and finally one part in the presence of an association of androstanolone and the test product.

At the moment of the placing of the prostatic explants in the culture, 1μ Ci of $H^3$-Thymidine (26 Ci/mmole) was added to the medium in aqueous solution with a volume of 0.1 ml. After 72 hours of culture, the explants were rinsed and homogenized with a Potter homogenizer in a solution of 0.25 M of saccharose containing 1.5 mM of $CaCl_2$. The activity of the alkaline phosphatase was determined at a pH of 10.5 with the method of Bessey et al [J. Biol. Chem., Vol. 164, p. 321] with the surnageant of centrifugation of the homogenate explants.

To measure the incorporation of $H^3$-Thymidine to desoxyribonuclecic acid (ADN), the centrifugation culot was taken up in 1 ml of normal sodium hydroxide for one hour at 37° C and then was washed 3 times with 4 ml of 5% of trichloroacetic acid. The radioactivity of the centrifugation culot was measured after being taken up in 0.5 ml of Soluene R. The results were expressed in dpm of $H^3$-Thymidine incorporated into ADN per mg of tissue. The antagonism of the effects provoked by androstanolone (increase in alkaline phosphatase activity and incorporation of $H^3$-Thymidine in ADN) demonstrated the local antiandrogenic activity of the test product and the results are reported in Table II.

TABLE II

| Groups | Concentration in M | Alkaline Phosphatase mU/mg | $H^3$-Thymidine incorporation kpm/mg |
|---|---|---|---|
| Controls | — | 52 | 208 |
| Androstanolone | $5 \times 10^{-8}$ | 108 | 724 |
| Androstanolone + product of Example 3 | $5 \times 10^{-8}$ + $1 \times 10^{-6}$ | 86 | 343 |
| Controls | — | 40 | 458 |
| Androstanolone | $5 \times 10^{-8}$ | 90 | 874 |
| Androstanolone + product | $5 \times 10^{-8}$ | | |

TABLE II-continued

| Groups | Concentration in M | Alkaline Phosphatase mU/mg | H³-Thymidine incorporation kpm/mg |
|---|---|---|---|
| A | + 1 × 10⁻⁶ | 68 | 511 |

The product of Example 3 provoked a 74% inhibition of hormone incorporation while product A provoked a 87% inhibition of hormone incorporation.

C. Antiandrogenic Activity by topical administration on costovertebral sebaceous organ of hamsters Syrian hamsters (Mesocricetus auratus) presents at the level of dorsal skin two sebaceous formations on both sides of the vertebral column whose development is andro genodependent. Local treatment of these organs by daily application of a lotion containing an antiandrogen inhibits the weight increase of the costovertebral organ of the female provoked by the simultaneous subcutaneous administration of testosterone propionate. Observation of untreated controlateral organ permits an evaluation of the secondary antiandrogenic effect.

Lots of 5 female hamsters weighing 110 to 130 g received a daily treatment for 14 days. One group received subcutaneously testosterone propionate solubilized in sesame oil containing 5% benzyl alcohol at a dose of 0.2 ml/hamster/day (corresponding to 125 μg of testosterone propionate per day). Another group received simultaneously in addition to the same treatment a local treatment of the right costovertebral organ with 0.2 ml of a solution containing 25% by weight of the product of Example 3, 30% by weight of propylene carbonate, 37% by weight of ethanol and 8% by weight of Eutanol (5 mg of the product of Example 3/day.) The animals were killed 24 hours after the last treatment and the costovertebral organs were removed and weighed. The results are reported in Table III.

TABLE III

| Treatments | Weight of costovertebral organs in mg | |
|---|---|---|
| | Left | Right (Treated) |
| Controls | 9.6 ± 1.1 | 9.2 ± 1.2 |
| Testosterone propionate | 48.8 ± 2.7 | 43.3 ± 4.4 |
| Testosterone propionate + Product of Example 3 | 41.8 ± 3.3 | 25.4 ± 2.4 |

The local application of the product of Example 3 on the right costovertebral organ caused an non-significant variation of weight increase of the left costovertebral organ. This local application caused a 52% of inhibition of weight increase of the right organ. The product therefore locally antagonizes testosterone propionate without presenting secondary antiandrogenic effects.

Various modifications of the products and method of the invention may be made without departing from the spirit or scope thereof and it should be understood that the invention is to be limited only as defined in the appended claims.

We claim:

1. A method of treating symptoms of hyperandrogenicity in warm-blooded animals comprising topically applying to the skin or mucous of warm blooded animals an antiandrogenically effective amount of a compound of the formula

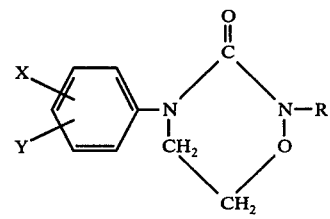

wherein X and Y are individually selected from the group consisting of hydrogen, halogen, —CF₃, —NO₃ and alkylthio of 1 to 4 carbon atoms and R is selected from the group consisting of hydrogen, alkyl of 1 to 6 carbon atoms, phenyl, benzyl and hydroxymethyl.

2. The method of claim 1 wherein R is methyl and X and Y are individually selected from the group consisting of chlorine, —CF₃ and —NO₂.

3. The method of claim 1 wherein the oxadiazine is 2-methyl-4-(3',4'-dichlorophenyl)-3-oxo-5,6-dihydro-1,2,4-oxadiazine.

4. The method of claim 1 wherein the oxadiazine is 2-methyl-4-(3'-trifluoromethyl-4'-nitrophenyl)-3-oxo-5,6-dihydro-1,2,4-oxadiazine.

* * * * *